(12) United States Patent
Adam et al.

(10) Patent No.: US 7,501,470 B2
(45) Date of Patent: Mar. 10, 2009

(54) USE OF POLYOXYPROPYLENE AND POLYOXYETHYLENE TERPENE COMPOUNDS IN EMULSION POLYMERIZATION

(75) Inventors: Herve Adam, Princeton, NJ (US); Jon D. Kiplinger, Columbus, NJ (US); Robert J. Tillotson, Toms River, NJ (US); Jean-Luc Joye, Hoboken, NJ (US); Hui Shirley Yang, Plainsboro, NJ (US)

(73) Assignee: Rhodia Inc., Cranbury, NJ (US)

( * ) Notice: Subject to any disclaimer, the term of this patent is extended or adjusted under 35 U.S.C. 154(b) by 37 days.

(21) Appl. No.: 11/291,752

(22) Filed: Dec. 1, 2005

(65) Prior Publication Data
US 2006/0135683 A1 Jun. 22, 2006

Related U.S. Application Data

(60) Provisional application No. 60/633,050, filed on Dec. 3, 2004.

(51) Int. Cl.
*C08L 31/00* (2006.01)
*C11D 1/722* (2006.01)
*C11D 17/08* (2006.01)
*C11D 17/00* (2006.01)

(52) U.S. Cl. ............... 524/556; 510/102; 510/107; 510/506; 510/245; 510/271; 526/303.1; 526/319; 516/30; 516/76; 524/555

(58) Field of Classification Search ............... 510/102, 510/107, 506, 245, 271, 421; 526/303.1, 526/319; 516/30, 76; 524/556, 555
See application file for complete search history.

(56) References Cited

U.S. PATENT DOCUMENTS

| 5,674,823 A * | 10/1997 | Ricca et al. ............ 510/102 |
| 5,770,760 A * | 6/1998 | Robinson ............... 560/221 |
| 6,476,168 B1 * | 11/2002 | Dahanayake et al. ..... 526/303.1 |
| 2002/0035052 A1 * | 3/2002 | Joye et al. ............. 510/245 |
| 2003/0054972 A1 * | 3/2003 | Joye et al. ............. 510/506 |

OTHER PUBLICATIONS

U.S. Appl. No. 10/820,929, filed Apr. 8, 2004, Joye et al.

* cited by examiner

*Primary Examiner*—Randy Gulakowski
*Assistant Examiner*—Michael M Bernshteyn

(57) ABSTRACT

The invention relates to the use, in emulsion polymerization, of at least a compound derived from a terpene and comprising a number of oxypropylene units ranging between 0 to 20, and a number of oxyethylene units ranging between 2 to 80.

18 Claims, No Drawings

USE OF POLYOXYPROPYLENE AND POLYOXYETHYLENE TERPENE COMPOUNDS IN EMULSION POLYMERIZATION

This patent application claims priority from provisional patent application Ser. No. 60/633,050 filed on Dec. 3, 2004.

FIELD OF THE INVENTION

The present invention relates to emulsion polymerization using terpene based surfactants as emulsifiers. The terpene based surfactants comprise oxypropylene and oxyethylene units. The invention also relates to emulsion polymerization using the sulfate and phosphate salts of the terpene based surfactants as emulsifiers. Further, the present invention relates to methods of using such emulsions formed from the terpene based surfactants.

BACKGROUND OF THE INVENTION

Polymers, both synthetic and natural, have been employed in aqueous solutions as thickening and flocculating agents. They have found commercial use in a variety of end uses such as wastewater treatment, water purification, papermaking, petroleum recovery, oil drilling mud stabilizers, and latex. Latex is a water based polymer dispersion, widely used in industrial applications.

Polymerization is a preferred technology used to make emulsion polymers and polymer latexes. The use of latex, produced by emulsion polymerization, in the production of paints or coatings for substrates is well known in the art. However, such paints or coatings are adversely affected by the presence of emulsifiers required in the emulsion polymerization process. The emulsifiers often cause foaming in the paint or coating. It would be desirable to have an emulsifier having low foaming effects and improved stability properties.

Furthermore, in latex polymerization, surfactants are necessary to provide stable monomer pre-emulsion, stability during the polymerization, and overall stability of the final latex. However, traditional surfactants for polymerization of latexes and emulsions tend to create foaming upon agitation and cause other difficulties during the polymerization process and in the final formulations containing the latex. To overcome this, a defoamer is generally required. Unfortunately, addition of a defoamer has numerous drawbacks including dewetting of the coating and increased raw material cost. It would be desirable to have a polymerization surfactant having low foaming effects and improved stability properties.

SUMMARY OF THE INVENTION

This invention provides a process for the production of polyoxypropylene and polyoxyethylene terpene based surfactants, and processes to produce emulsion polymers of such polyoxypropylene and polyoxyethylene terpene based surfactants and the resulting emulsion polymer products. The polyoxypropylene and polyoxyethylene terpene based surfactants produced by the process of this invention produce emulsion polymers of greatly improved properties compared to emulsion polymers produced from conventional surfactants.

Particularly, the invention is directed to the use of polyoxypropylene and polyoxyethylene terpene based surfactants for latex synthesis. More particularly, the invention is directed to the use of alkoxylate surfactants and their sulfate and phosphate salts useful in emulsion and latex synthesis. Even more particularly, the invention is directed to the use of alkoxylates of 6,6-dimethylbicyclo[3,1,1]hept-2-ene-2-ethanol and their sulfate and phosphate salts as emulsifiers useful in emulsion and latex polymerization.

Furthermore, the polyoxypropylene and polyoxyethylene terpene based surfactants may be nonionic or anionic.

DETAILED DESCRIPTION OF INVENTION AND PREFERRED EMBODIMENTS

The present invention relates to the use, in emulsion polymerization, of a terpene based surfactant. The terpene based surfactant in accordance with the invention comprises at least one compound having the following formula:

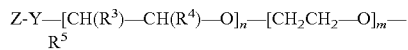

in which Z represents a bicyclo[a,b,c,]heptenyl or bicyclo[a,b,c]heptyl radical, and wherein a+b+c=5 and a=2, 3, or 4; b=2 or 1; and c=0 or 1. $R^3$ and $R^4$, which may be identical or different, represent hydrogen or a linear, branched or cyclic, saturated or unsaturated $C_1$-$C_{22}$ hydrocarbon radical, provided that at least one of the radicals $R^3$ or $R^4$ is other than hydrogen; and $R^5$ represents hydrogen, or a group selected from the following:

—$SO_3M$

—$PO_3(M)_2$

—$(CH_2)_r$—COOM

—$(CH_2)_n$—$SO_3M$ in which formula, M represents hydrogen, an alkali metal or an ammonium function $N(R)_4+$, in which R, which may or may not be identical, represents hydrogen or a linear, branched or cyclic, saturated or unsaturated $C_1$-$C_{22}$ hydrocarbon radical, which may be hydroxylated; r is in the range 1 to 6; z is in the range 1 to 6; n is a whole number or fraction in the range 0-20 inclusive; m is a whole number or fraction in the range 2-80 inclusive.

The Z radical is optionally substituted by at least one $C_1$-$C_6$ alkyl radical and may comprise a backbone selected from those indicated below or the corresponding backbones minus the double bond:

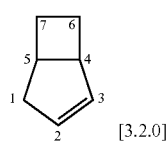

a)

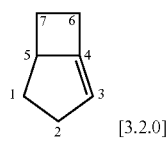

b)

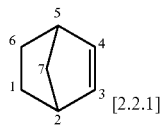

c)

-continued

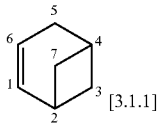
d)

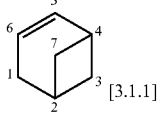
e)

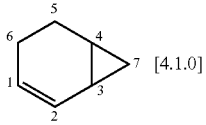
f)

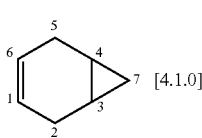
g)

Y represents —$CH_2$—$C(R^1)(R^2)$—O— or —O—$CH(R'^1)$—$CH(R'^2)$—O—, wherein $R^1$, $R^2$, $R'^1$, $R'^2$, which may be identical or different, represent hydrogen or a linear, branched or cyclic, saturated or unsaturated $C_1$-$C_{22}$ hydrocarbon radical, preferably $C_1$-$C_6$ In a preferred embodiment of the invention a suitable terpene based surfactant comprises the use of Nopol derivative surfactants. Accordingly, the invention further provides for the novel use of Nopol derivative surfactants to make emulsion polymers or polymer latexes. In one aspect, this invention relates to a method of making Nopol alkoxylate surfactants of 6,6-dimethylbicyclo[3,1,1]hept-2-ene-2-ethanol. The alkoxylate surfactants may be nonionic or anionic. The anionic alkoxylate surfactants are preferably sulfates or phosphates of the 6,6-dimethylbicyclo[3,1,1]hept-2-ene-2-ethanol alkoxylate. Suitable alkoxylate compounds are described in U.S. patent application Ser. No. 10/820,929, which is herein incorporated by reference.

Preferred alkoxylated surfactants have the general formula:

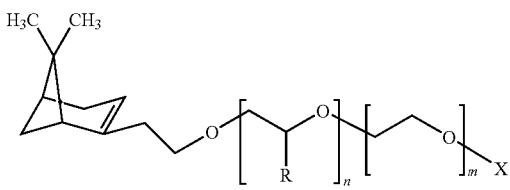
(I)

where R is hydrogen, $CH_3$, or $C_2H_5$; n is from 0 to 20 inclusive, m is from 2 to 80 inclusive; and X represents a hydrogen atom, phosphate, sulfate, sulphonate, or carboxylate group. The moiety qualified by the integer "n" corresponds to oxypropylene units. Oxypropylene can also be substituted by oxybutylene or similar alkoxylates. The moiety qualified by the integer "m" corresponds to oxyethylene units. The oxypropylene and oxyethylene units may be of block distribution or intermixed in random or tapered distribution along the chain. The compounds of the formula may also be described as alkoxylates of 6,6-dimethylbicyclo[3.1.1]hept-2-ene-2-ethanol.

Preferred anionic alkoxylated surfactants have the general formula above wherein X represents a sulfate or phosphate group, and preferred nonionic alkoxylated surfactants have the general formula above wherein X represents a hydrogen group.

The terpene based surfactants described above are used in latex emulsion polymers or as emulsifiers/surfactants in emulsion polymerization. Latex, water based dispersions of polymers obtained by emulsion polymerization, are widely used in various applications such as paints, adhesives, paper coatings, carpet backing and rheology modifiers (HASE).

As discussed previously, the surfactants used to stabilize the latex can increase foaming during the manufacturing of the latex and in the final application and require the addition of a defoamer that may have other inconveniences such as the dewetting of the coating responsible for the formation of fish eyes in the paint film. The foaming phenomenon is also detrimental to paint quality and should be avoided. The terpene based surfactant of this invention may be used as replacements for traditional foamy emulsifiers employed in emulsion polymerization and eliminate or avoid the problem or drawbacks in the resulting latex and its final applications such as paints, coatings, adhesives, or rheology modifiers.

In another aspect, this invention relates to a method of making an emulsion polymer by emulsion polymerization in the presence of a terpene based surfactant. For example, an emulsion polymer is produced by emulsion polymerization in the presence of a Nopol surfactant having the formula:

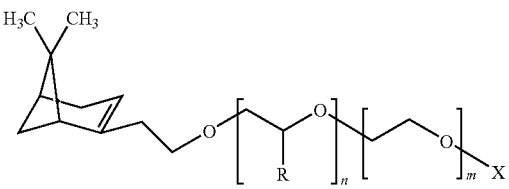

where R is hydrogen, $CH_3$ or $C_2H_5$.

The Nopol surfactant can be made by different routes. For example, a preferred surfactant wherein X is a sulfate, for example, —$OSO_3H_2$, group can be made by sulfation of the product of esterification of a 6,6 dimethylbicyclo [3,1,1]hept-2-ene-2-ethanol alkoxylate. A Nopol surfactant wherein X is a sulfate —$OSO_3H_2$ group or sulfonate —$SO_3H$ group, can be made by sulfating one of the hydroxyl groups of the alkoxylate, or replacing the hydroxyl group with a sulfonate group, and then esterifying the remaining hydroxyl group of the alkoxylate with a vinyl-functional carboxylic acid, anhydride, or acid halide thereof.

Emulsion polymerization is discussed in G. Pohlein, "Emulsion Polymerization", Encyclopedia of Polymer Science and Engineering, vol. 6, pp. 1-51 (John Wiley & Sons, Inc., N.Y., N.Y., 1986), the disclosure of which is incorporated herein by reference. Emulsion polymerization is a heterogeneous reaction process in which unsaturated monomers or monomer solutions are dispersed in a continuous phase with the aid of an emulsifier system and polymerized with free-radical or redox initiators. The product, a colloidal dispersion of the polymer or polymer solution, is called a latex.

The comonomers which are typically employed include such monomers as methyl acrylate, ethyl acrylate, methyl methacrylate, butyl acrylate, 2-ethyl hexyl acrylate, other acrylates, methacrylates and their blends, acrylic acid, methacrylic acid, styrene, vinyl toluene, vinyl acetate, vinyl esters of higher carboxylic acids than acetic acid, e.g. vinyl versatate, acrylonitrile, acrylamide, butadiene, ethylene, vinyl chloride and the like, and mixtures thereof.

In the above process, suitable initiators, reducing agents, catalysts and surfactants are well known in the art of emulsion polymerization. Typical initiators include ammonium persulfate (APS), hydrogen peroxide, sodium, potassium or ammonium peroxydisulfate, dibenzoyl peroxide, lauryl peroxide, ditertiary butyl peroxide, 2,2'-azobisisobutyronitrile, t-butyl hydroperoxide, benzoyl peroxide, and the like.

Suitable reducing agents are those which increase the rate of polymerization and include for example, sodium bisulfite, sodium hydrosulfite, sodium formaldehyde sulfoxylate, ascorbic acid, isoascorbic acid, and mixtures thereof.

Suitable catalysts are those compounds which increase the rate of polymerization and which, in combination with the above-described reducing agents, promote decomposition of the polymerization initiator under the reaction conditions. Suitable catalysts include transition metal compounds such as, for example, ferrous sulfate heptahydrate, ferrous chloride, cupric sulfate, cupric chloride, cobalt acetate, cobaltous sulfate, and mixtures thereof.

Suitable surfactants which may be used in conjunction with the Nopol surfactant include ionic and nonionic surfactants such as alkyl polyglycol ethers such as ethoxylation products of lauryl, tridecyl, oleyl, and stearyl alcohols; alkyl phenol polyglycol ethers such as ethoxylation products of octyl- or nonylphenol, diisopropyl phenol, triisopropyl phenol; alkali metal or ammonium salts of alkyl, aryl or alkylaryl sulfonates, sulfates, phosphates, and the like, including sodium lauryl sulfate, sodium octylphenol glycolether sulfate, sodium dodecylbenzene sulfonate, sodium lauryldiglycol sulfate, and ammonium tritertiarybutyl phenol and penta- and octa-glycol sulfonates, sulfosuccinate salts such as disodium ethoxylated nonylphenol half ester of sulfosuccinic acid, disodium n-octyldecyl sulfosuccinate, sodium dioctyl sulfosuccinate, and the like.

A typical process of emulsion polymerization preferably involves charging water to a reactor and feeding as separate streams a pre-emulsion of the monomer and a solution of the initiator. A small amount of the pre-emulsion and a portion of the initiator may be charged initially at the reaction temperature to produce a "seed" latex. The "seed" latex procedure results in better particle-size reproducibility. Under "normal" initiation conditions, that is initiation conditions under which the initiator is activated by heat, the polymerization is normally carried out at about 60-90° C. A typical "normal" initiated process, for example, could employ ammonium persulfate as initiator at a reaction temperature of 80+/−2° C. Under "redox" initiation conditions, that is initiation conditions under which the initiator is activated by a reducing agent, the polymerization is normally carried out at 60-70° C. Normally, the reducing agent is added as a separate solution. A typical "redox" initiated process, for example, could employ potassium persulfate as the initiator and sodium metabisulfite as the reducing agent at a reaction temperature of 65+/−2° C.

In the above emulsions, the polymer preferably exists as a generally spherical particle, dispersed in water, with a diameter of about 50 nanometers to about 500 nanometers.

In particular, the terpene based surfactants of this invention may be incorporated in effective amounts in aqueous polymer systems to enhance the stability of emulsions of the polymers. Commonly used monomers in making acrylic paints are butyl acrylate, methyl methacrylate, ethyl acrylate and the like. In acrylic paint compositions the polymer is comprised of one or more esters of acrylic or methacrylic acid, typically a mixture, e.g. about 50/50 by weight, of a high $T_g$ monomer (e.g. methyl methacrylate) and a low $T_g$ monomer (e.g. butyl acrylate), with small proportions, e.g. about 0.5% to about 2% by weight, of acrylic or methacrylic acid. The vinyl-acrylic paints usually include vinyl acetate and butyl acrylate and/or 2-ethyl hexyl acrylate and/or vinyl versatate. In vinyl-acrylic paint compositions, at least 50% of the polymer formed is comprised of vinyl acetate, with the remainder being selected from the esters of acrylic or methacrylic acid. The styrene/acrylic polymers are typically similar to the acrylic polymers, with styrene substituted for all or a portion of the methacrylate monomer thereof.

In order to further illustrate the invention and the advantages thereof, the following non-limiting examples are given.

EXAMPLES

Example 1

Latex trials 1 to 13 were prepared using the following formulation:

| Description: Acrylic Pressure Sensitive Adhesive Latex Total Solids (by formula): 55% | | | |
|---|---|---|---|
| | Formula Wt (g) | Active Wt (g) | % BOTM[1] |
| Kettle Charge | | | |
| Deionized Water | 191.50 | 0.00 | 0.00% |
| Sodium Bicarbonate | 0.55 | 0.55 | 0.10% |
| | 192.05 | 0.55 | |
| Monomer Emulsion | | | |
| Deionized Water | 154.1 | 0.00 | 0.00% |
| Surfactant | 5.50 | 3.19 | 0.58% |
| Butyl acrylate | 533.5 | 533.50 | 97.00% |
| Hydroxyethyl acrylate | 11.0 | 11.00 | 2.00% |
| Acrylic acid | 5.5 | 5.50 | 1.00% |
| | 709.6 | 553.19 | |
| | | 550.0 = grams total monomer | |
| Initiator Solution | | | |
| Deionized Water | 107.0 | 0.00 | 0.00% |
| Ammonium Persulfate | 2.2 | 2.20 | 0.40% |
| | 109.2 | 2.20 | |
| Total | 1010.8 | 555.94 | |
| Reactor setup: | 1200 ml 2 piece glass kettle reactor Overhead mixer with glass shaft/Teflon paddle blade | | |

PROCEDURE

1. Heat kettle charge to 80° C. while purging with nitrogen. Maintain nitrogen purge throughout run.
   Adjust agitation for homogeneous mixing throughout run.
2. Add 5% of monomer emulsion (35.5 g). Wait 5 minutes for temperature to rebound.
3. Add 25% (27.3 g) of initiator solution and hold at 80° C. for 15 minutes.
4. Feed the remainder of monomer emulsion and initiator solution over a 2.5-3 hour period.
5. Maintain the reaction temperature at 80° C. throughout the feeds.
6. After addition, heat to 85° C. and hold for 30 minutes.
7. Cool to below 30° C., adjust pH to 8 ± 0.2 with NH4OH and filter through 100 mesh screen.

[1]% based on total monomer concentration

Surfactant substitutions and changes in surfactant percent concentrations, were as indicated in the following trials.

TABLE 1

Latex trials comparing control surfactant to Nopol propoxy (PO)/ethoxy (EO) sulfate as indicated:

| | Trial # | | | | |
|---|---|---|---|---|---|
| Surfactant Substitution | 1 Control Rhodapex CO-436 | 2 Nopol 3PO/2.5EO Sulfate NH4+ | 3 Nopol 5PO/3EO Sulfate, NH4+ | 4 Nopol 5PO/5EO Sulfate, NH4+ | 5 Nopol 5PO/7EO Sulfate, NH4+ |
| % BOTM Total Surfactant | 0.58 | 0.58 | 0.58 | 0.58 | 0.58 |
| % BOTM Surfactant in Kettle Charge | 0.0 | 0.0 | 0.0 | 0.0 | 0.0 |
| % Wet Coagulum (BOTL) | 0.05 | 0.01 | 0.03 | 0.05 | 0.14 |
| % Wet Grit (100 mesh BOTL) | trace | trace | 0.01 | 0.01 | 0.04 |
| % Total Solids | 54.39 | 54.2 | 54.3 | 54.2 | 54.3 |
| % Conversion | 98.9 | 98.5 | 98.8 | 98.5 | 98.7 |
| Mean Particle Diameter/Std Dev (nm) | 292.1/40 | 406.7/35.1 | 364.7/34.7 | 361.1/49.7 | 400.8/60.3 |
| pH | 2.0 | 2.3 | 2.6 | 2.4 | 2.5 |
| Viscosity (cP) at Room Temp | 140 | 67.5 | 85 | 70 | 85 |
| Freeze/Thaw # cycles | 0 | 0 | 0 | 0 | 0 |
| 60° C. Oven Stability | Pass 30 days | Pass 30 days | Pass 30 days | Pass 30 days | Pass 30 days |

BOTM = Based on total monomer
BOTL = Based on total liquid
nm = Nanometer
cP = Centipoise units
Rhodapex CO-436 ® (commercially available from Rhodia Inc.) is a sulfated alkyl phenol ethoxylate surfactant.

Table 1 results showed that similar latex properties can be achieved with Nopol PO/EO sulfates of several different molecular weight ranges.

TABLE 2

Latex trials comparing control surfactant to Nopol propoxy (PO)/ethoxy (EO) sulfate as indicated:

| | Trial # | | | |
|---|---|---|---|---|
| Surfactant substitution | 6 Control Rhodapex CO-436 | 7 Nopol 5PO/3EO Sulfate, NH$_4$+ | 8 Nopol 5PO/5EO Sulfate, NH4+ | 9 Nopol 5PO/7EO Sulfate, NH$_4$+ |
| % BOTM Total Surfactant | 0.58 | 0.58 | 0.58 | 0.58 |
| % BOTM Surfactant in Kettle Charge | 0 | 0.025 | 0.03 | 0.03 |
| % Wet Coagulum (BOTL) | 0.05 | 0.05 | 0.08 | 0.06 |
| % Wet Grit (100 mesh BOTL) | Trace | Trace | 0.01 | 0.11 |
| % Total Solids | 54.4 | 54.2 | 54.2 | 53.7 |
| % Conversion | 98.9 | 98.6 | 98.6 | 97.7 |
| Mean Particle Diameter/Std Deviation (nm) | 292/40 | 260/32 | 257/23 | 288/19 |
| pH | 2.0 | 2.4 | 2.4 | 2.7 |
| Viscosity (cP) at Room Temp | 78 | 88 | 80 | 85 |

BOTM = Based on total monomer
BOTL = Based on total liquid
nm = Nanometer
cP = Centipoise units
Rhodapex CO-436 is a commercially available sulfated alkyl phenol ethoxylate surfactant from Rhodia.

The results shown in Table 2 indicate that similar latex properties can be achieved with Nopol PO/EO sulfates of several different molecular weight ranges. Table 2 further illustrates the effect of adding Nopol PO/EO sulfate to the kettle charge and the ability to vary the particle size in the final latex (compare to Table 1).

Trials 7-9 were performed to "tune" the particle size of the Nopol PO/EO sulfate so that they were in the 250-300 nm range. Rhodapex CO-436 (trial # 6) was also in the 250-300 nm range. The particle size was controlled so as not to cause interference or variations in tests that can be affected by particle size variation, such as freeze/thaw, foaming, Ca++ and mechanical stability.

TABLE 3

Latex trials comparing control surfactant to Nopol propoxy (PO)/ethoxy (EO) sulfate as indicated:

| | Trial # | | | |
|---|---|---|---|---|
| Surfactant substitution | 6 Control Rhodapex CO-436 | 7 Nopol 5PO/3EO Sulfate, NH$_4$+ | 8 Nopol 5PO/5EO Sulfate, NH4+ | 9 Nopol 5PO/7EO Sulfate, NH$_4$+ |
| Ca++ Stability Test (highest concentration passed) | Passed (0.01 M) | Passed (0.01 M) | Passed (0.01 M) | Passed (0.01 M) |
| Foam Test - Initial Height (ml) | 42 | 28 | 28 | 30 |
| Foam test - Height after 5 minutes (ml) | 40 | 26 | 25 | 24 |
| Foam test - Height after 15 minutes (ml) | 40 | 23 | 21 | 22 |
| Mechanical Stability (Waring Blender 20,000 rpm for 5 minutes) | Passed | Passed | Passed | Passed |

TABLE 3-continued

Latex trials comparing control surfactant to Nopol propoxy (PO)/ethoxy (EO) sulfate as indicated:

| | Trial # | | | |
|---|---|---|---|---|
| | 6 | 7 | 8 | 9 |
| Surfactant substitution | Control Rhodapex CO-436 | Nopol 5PO/3EO Sulfate, $NH_4+$ | Nopol 5PO/5EO Sulfate, NH4+ | Nopol 5PO/7EO Sulfate, $NH_4+$ |
| Surface tension (dynes/cm) | 39.01 | 43.05 | 42.05 | 41.19 |
| Film Aspect | Good clear film | Good clear film | Good clear film | Good clear film |
| F/T (# cycles) stability | (0) | (0) | (0) | (0) |
| 60° C. Oven Stability | Pass 30 days | Pass 30 days | Pass 30 days | Pass 30 days |

M = molar

The results in Table 3 continue to show that Nopol PO/EO sulfates of several different molecular weights produce similar latex properties such as mechanical, chemical and temperature stability, film quality and surface tension, compared to the control surfactant. Film aspect was excellent for all latexes tested in Table 3, yielding draw downs that are clear and free of defects. No observable difference was seen between the control and Nopol PO/EO sulfate latex films. The results in Table 3 also illustrate that Nopol PO/EO sulfates of several different molecular weights can be used to produce latex with lower foaming properties, as seen in lower initial foam height as well as lower foam height over time.

TABLE 4

Adhesion results: 180° Peel and Loop Tack Testing

| Trial # | Description | Loop Tack (Max Load-N) | 180° Peel (N/cm) |
|---|---|---|---|
| 6 | Control latex made with Rhodapex CO-436 | 9.80 | 2.19 |
| 7 | Latex made with Nopol 5PO/3EO Sulfate | 11.06 | 2.41 |
| 8 | Latex made with Nopol 5PO/5EO Sulfate | 13.34 | 2.81 |
| 9 | Latex made with Nopol 5PO/7EO Sulfate | 13.18 | 2.66 |

Four PSA latexes were tested for peel and tack properties. The latex trials tested are described in Table 2.

Loop Tack Testing:

Samples were prepared by drawing down the neutralized latex onto PET film with a 3 mil 3" drawdown bar. The draw downs were allowed to air dry, and were oven cured at 105° C. for 5 minutes prior to covering the film with release paper. A 1" wide strip was cut from the PET/adhesive/release paper "sandwich" and cut to 7" long with the adhesive in the center for loop tack testing. The ends were taped for the grips, and the testing was performed by lowering the adhesive coated PET film strip to 1" from the SS test surface. The 1" setting ensures that each sample is forced against the SS surface with the same pressure. The Instron Tensiometer® was used to pull the loop up at 12"/minute, and the peak force required to remove the loop was recorded.

180° Peel Test:

The sample prep was a little different for the peel test, in that the drawdown was done at the low end of the PET film, as opposed to the center. This was done so that a long "tail" of PET was left for the upper grip to grab for the peel test. Standard SS substrates were used and the pressure applied to the adhesive coated PET film was kept uniform by using a standard roller for the same number of passes at approximately the same speed.

Generally, strong tack and good resistance to peel is desired in pressure sensitive adhesive latexes, and both properties can potentially be impacted by the surfactant used to make the latex.

The data in Table 4 summarizes the results of the 180° peel and loop tack testing. Multiple replications were performed for each sample. The Nopol sulfate latexes showed equivalent or better performance vs. the control.

TABLE 5

Latex trials with Nopol propoxy (PO)/ethoxy (EO) sulfate as indicated:

| | Trial # | | | |
|---|---|---|---|---|
| | 10 | 11 | 12 | 13 |
| Surfactant Substitution | Nopol 5PO/19EO Sulfate $NH_4+$ | Nopol 5PO/19EO Sulfate NH4+ | Nopol 5PO/25EO Sulfate, NH4+ | Nopol 5PO/25EO Sulfate, NH4+ |
| % BOTM Total Surfactant | 0.58 | 0.58 | 0.58 | 0.58 |
| % BOTM Surfactant in Kettle Charge | 0 | 0.06 | 0 | 0.06 |
| % Wet Coagulum (BOTL) | 0.11 | 0.09 | 0.06 | 0.10 |
| % Wet Grit (100 mesh BOTL | 0.03 | 0.10 | 0.04 | 1.27 |
| % Total Solids | 54.4 | 54.2 | 54.4 | 53.6 |
| % Conversion | 98.9 | 98.6 | 98.9 | 97.4 |
| Mean Particle Diameter/Std Dev (nm) | 449/43 | 256/28 | 457/71 | 408/76 |
| pH | 2.6 | 2.9 | 2.5 | 2.7 |
| Viscosity (cP) at Room Temp | 73 | 78 | 65 | 70 |

BOTM = Based on total monomer
BOTL = Based on total liquid
nm = Nanometer
cP = Centipoise units
SS = stainless steel
PET = Polyethylene Terephthalate The results shown in Table 5 show that similar latex properties can be achieved with Nopol PO/EO sulfates of several different molecular weight ranges, compared to the control surfactant. Table 5 illustrates the effect of adding Nopol PO/EO sulfate to the kettle charge and the ability to vary the particle size in the final latex.

Example 2

Latex trials 14 to 27 were prepared using the following formula:

| Description: Acrylic Paint Latex Total Solids (by formula): 51% | | | |
|---|---|---|---|
| | Formula wt (g) | Active Wt (g) | % BOTM[1] |
| Kettle Charge | | | |
| Deionized Water | 191.22 | 0.00 | 0.00% |
| Surfactant | 1.74 | 1.02 | 0.20% |
| | 192.96 | 1.02 | |
| Monomer Emulsion | | | |
| Deionized Water | 191.67 | 0.00 | 0.00% |
| Surfactant | 15.37 | 9.02 | 1.80% |
| Methyl methacrylate | 260.00 | 260.00 | 52.00% |
| Butyl acrylate | 235.00 | 235.00 | 47.00% |
| Methacrylic acid | 5.00 | 5.00 | 1.00% |
| | 707.04 | 509.02 | |
| | | 500.00 = grams total monomer | |
| Initiator Solution | | | |
| Deionized Water | 98.00 | 0.00 | 0.00% |
| Ammonium Persulfate | 2.00 | 2.00 | 0.40% |
| | 100.00 | 2.00 | |
| Total | 1000.00 | 512.04 | |
| Reactor setup: | 1200 ml 2 piece glass kettle reactor | | |
| | Overhead mixer with glass shaft/Teflon paddle blade | | |

PROCEDURE

1. Heat kettle charge to 82° C. while purging with nitrogen. Maintain nitrogen purge throughout run. Adjust agitation for homogeneous mixing throughout run.
2. Add 2% of monomer emulsion (14.14 g). Wait 5 minutes for temperature to rebound.
3. Add 25% (25.0 g) of initiator solution and hold at 80° C. for 15 minutes.
4. Feed the remainder of monomer emulsion and initiator solution over a 2.5-3 hour period.
5. Maintain the reaction temperature at 80° C. throughout the feeds.
6. After addition, heat to 85° C. and hold for 30 minutes.
7. Cool to below 30° C., adjust pH to 9 with NH4OH and filter through 100 mesh screen.

[1]% based on total monomer concentration

Surfactant substitutions and changes in surfactant percent concentrations, were as indicated in the following trials.

TABLE 6

Latex trials comparing control surfactants to Nopol propoxy (PO)/ethoxy (EO) sulfate as indicated:

| | Trial # | | | |
|---|---|---|---|---|
| | 14 | 15 | 16 | 17 |
| Surfactant Substitution | Control Rhodapex CO-436 | Control Rhodapex AB-20 | Control Rhodapex LA-40/S | Nopol 5PO 7EO sulfate |
| % BOTM Total Surfactant | 2.00 | 2.00 | 2.00 | 2.00 |
| % BOTM Surfactant in Kettle charge | 0.20 | 0.20 | 0.20 | 0.20 |
| Wet Coagulum, % BOTL | 0.01 | 0.03 | 0.48 | 0.06 |
| Wet Grit, % BOTL | 0.04 | Nil | 1.08 | 0.01 |
| pH | 9.1 | 9 | 9 | 9 |
| Solids, % | 49.91 | 49.93 | 49.68 | 49.98 |
| Conversion, % | 97.48 | 97.71 | 97.2 | 97.77 |
| Particle Size | | | | |
| Mean Diameter, nm | 114.6 | 123.6 | 121.1 | 137.2 |
| Std. Deviation, nm | 20.2 | 18 | 8.8 | 21.3 |
| Std. Deviation, % | 17.6% | 14.5% | 7.3% | 15.5% |
| Viscosity, 25° C., cP | 457.9 | 565.9 | 535.9 | 300.9 |

BOTM = Based on total monomer
BOTL = Based on total liquid
nm = Nanometer
cP = Centipoise units
Rhodapex CO-436 is a commercially available sulfated alkyl phenol ethoxylate surfactant from Rhodia.
Rhodapex AB-20 is a commercially available sulfated alcohol ethoxylate from Rhodia.
Rhodapex LA-40/S is a commercially available sulfated alcohol ethoxylate from Rhodia.

Table 6 shows the latex properties of the Example 2 Nopol PO/EO sulfate formulation in comparison to three commercially available surfactants. Table 6 illustrates that similar latex properties were achieved with the Nopol PO/EO sulfate compared to the control commercial surfactants.

TABLE 7

Latex trials comparing Nopol propoxy (PO)/ethoxy (EO) sulfate as indicated:

| | Trial # | | | | |
|---|---|---|---|---|---|
| Surfactant Substitution | 18 Nopol 5PO 5EO sulfate | 19 Nopol 5PO 7EO sulfate | 20 Nopol 5PO 19EO sulfate | 21 Nopol 5PO 25EO sulfate | 22 Nopol 5PO 30EO sulfate |
| % BOTM Total Surfactant | 2.00 | 2.00 | 2.00 | 2.40 | 2.40 |
| % BOTM Surfactant in Kettle Charge | 0.20 | 0.20 | 0.20 | 0.20 | 0.20 |
| Wet Coagulum, % BOTL | 0.04 | 0.09 | 0.04 | 0.02 | 0.04 |
| Wet Grit, % BOTL | 0.16 | 0.01 | 0.01 | Nil | 0.02 |
| pH | 9 | 9 | 9 | 9 | 9 |
| Solids, % | 50 | 49.94 | 50.09 | 49.78 | 50.62 |
| Conversion, % | 97.8 | 97.72 | 97.83 | 97.01 | 98.47 |
| Particle Size | | | | | |
| Mean Diameter, nm | 149.5 | 147.7 | 162.5 | 191 | 176.2 |
| Std. Deviation, nm | 31.1 | 10.9 | 16.1 | 24.9 | 10 |
| Std. Deviation, % | 20.8% | 7.4% | 9.9% | 13.0% | 5.6% |
| Viscosity, 25° C., cP | 107 | 269 | 252 | 94 | 274.5 |

BOTM = Based on total monomer
BOTL = Based on total liquid
nm = Nanometer
cP = Centipoise units The Table 7 results show that similar latex properties can be achieved with Nopol PO/EO sulfates of several different molecular weight ranges, in comparison to the control surfactants (Table 6).

TABLE 8

Latex trials comparing control surfactants to Nopol propoxy (PO)/ethoxy (EO) sulfate as indicated:

| | Trial # | | | | |
|---|---|---|---|---|---|
| Surfactant Substitution | 23 Control Rhodapex CO-436 | 24 Control Rhodapex AB-20 | 25 Control Rhodapex LA-40/S | 26 Nopol 5PO 7EO sulfate | 27 Nopol 5PO 7EO sulfate |
| % BOTM Total Surfactant | 2.00 | 2.00 | 2.00 | 2.00 | 2.00 |
| % BOTM Surfactant in Kettle Charge | 0.05 | 0.15 | 0.10 | 0.20 | 0.20 |
| Wet Coagulum, % BOTL | 0.05 | 0.04 | 0.01 | 0.06 | 0.02 |
| Wet Grit, % BOTL | 0.06 | 0.08 | 0.02 | 0.01 | 0.01 |
| pH | 9 | 9 | 9 | 9 | 9 |
| Solids, % | 49.83 | 50.03 | 50.11 | 49.98 | 50.3 |
| Conversion, % | 97.32 | 97.71 | 97.72 | 97.77 | 98.4 |
| Particle Size | | | | | |
| Mean Diameter, nm | 140.6 | 153.1 | 143.2 | 137.21 | 145.6 |
| Std. Deviation, nm | 17 | 20.4 | 20.2 | 21.3 | 18.4 |
| Std. Deviation, % | 12.1% | 13.3% | 14.1% | 15.5% | 12.6% |
| Viscosity, 25° C., cP | 180.0 | 239.4 | 247.9 | 300.9 | 227.0 |
| Foam Test | | | | | |
| Initial Liquid volume, ml | 200 | 200 | 200 | 200 | 200 |
| Initial Foam Height, ml | 425 | 420 | 410 | 355 | 372.5 |

TABLE 8-continued

Latex trials comparing control surfactants to Nopol propoxy (PO)/ethoxy (EO) sulfate as indicated:

| | Trial # | | | | |
|---|---|---|---|---|---|
| Surfactant Substitution | 23 Control Rhodapex CO-436 | 24 Control Rhodapex AB-20 | 25 Control Rhodapex LA-40/S | 26 Nopol 5PO 7EO sulfate | 27 Nopol 5PO 7EO sulfate |
| Height after 5 minutes, ml | 425 | 415 | 400 | 350 | 370 |
| Height after 15 minutes, ml | 415 | 410 | 390 | 345 | 365 |
| Initial increase in volume, % | 113% | 110% | 105% | 78% | 86% |

BOTM = Based on total monomer
BOTL = Based on total liquid
nm = Nanometer
cP = Centipoise units
Rhodapex CO-436 is a commercially available sulfated alkyl phenol ethoxylate surfactant from Rhodia.
Rhodapex AB-20 is a commercially available sulfated alcohol ethoxylate from Rhodia.
Rhodapex LA-40/S is a commercially available sulfated alcohol ethoxylate from Rhodia.

The Table 8 results show that latex particle size can be adjusted ("tuned") by changing the amount of surfactant added upfront in the kettle charge while maintaining the same total amount of surfactant used in the polymerization. (See control surfactant trials in Table 6, for comparison.) When the control surfactants and Nopol PO/EO sulfate were adjusted to the same particle size range, as in Table 8, lower foaming results are achieved with the Nopol PO/EO sulfate in comparison to the commercially available surfactants.

Example 3

Latex trials 28 to 32 were prepared using the following formula:

Description: Vinyl Acrylic Paint Latex
Total Solids (by formula): 51.7%

| | Formula Wt (g) | Active Wt (g) | % BOTM[1] |
|---|---|---|---|
| Kettle Charge | | | |
| Deionized Water | 199.50 | 0.00 | 0.00% |
| Sodium Bicarbonate | 0.50 | 0.50 | 0.10% |
| | 200.00 | 0.50 | |
| Monomer Emulsion | | | |
| Deionized Water | 154.26 | 0.00 | 0.00% |
| Surfactant A | 25.85 | 7.50 | 1.50% |
| Surfactant B | 7.69 | 5.00 | 1.00% |
| Sodium Bicarbonate | 1.50 | 1.50 | 0.30% |
| Vinyl acetate | 400.00 | 400.00 | 80.00% |
| Butyl acrylate | 92.50 | 92.50 | 18.50% |
| Acrylic acid | 7.50 | 7.50 | 1.50% |
| | 689.30 | 514.00 500.00 = grams total monomer | |
| Initiator Solution | | | |
| Deionized Water | 98.00 | 0.00 | 0.00% |
| Sodium Persulfate | 2.00 | 2.00 | 0.40% |
| | 100.00 | 2.00 | |

Description: Vinyl Acrylic Paint Latex
Total Solids (by formula): 51.7%

| | Formula Wt (g) | Active Wt (g) | % BOTM[1] |
|---|---|---|---|
| Chaser Solutions | | | |
| Deionized Water | 5.00 | 0.00 | 0.00% |
| T-BHP (70%)[2] | 0.40 | 0.28 | 0.06% |
| | | 0.00 | 0.00% |
| Deionized Water | 5.00 | 0.00 | 0.00% |
| Isoascorbic acid | 0.30 | 0.30 | 0.06% |
| | | 0.00 | 0.00% |
| | 10.70 | 0.58 | |
| Total | 1000.00 | 517.08 | |
| Reactor setup: | 1200 ml 2 piece glass kettle reactor Overhead mixer with glass shaft/Teflon paddle blade | | |

PROCEDURE

1. Heat kettle charge to 80° C. while purging with nitrogen. Maintain nitrogen purge throughout run. Adjust agitation for homogeneous mixing throughout run.
2. Add 3% of monomer emulsion (20.68 g). Wait 5 minutes for temperature to rebound.
3. Add 25% (25.0 g) of initiator solution and hold at 80° C. for 15 minutes.
4. Feed the remainder of monomer emulsion for 3.75 hours and initiator solution for 4.25 hours.
5. Maintain the reaction temperature at 80° C. throughout the feeds.
6. After addition, hold at 80° C. for 15 minutes.
7. Cool reactor to 65° C. Add chaser solutions. Hold temperature at 63 +/− 2° C. for 20 minutes.
8. Cool to below 30° C., adjust pH to 7.0-7.5 with NH4OH and filter through 100 mesh screen.

[1]% based on total monomer concentration
[2]tert- butyl hydroperoxide, 70%

Surfactant substitutions and changes in surfactant percent concentrations, were as indicated in the following trials.

TABLE 9

Latex trials comparing control surfactants to Nopol propoxy (PO)/ethoxy (EO) sulfate as indicated:

| Trial # | 28 | 29 | 30 | 31 | 32 |
|---|---|---|---|---|---|
| Description | | | | | |
| Surfactant A | Control | Control | Nopol 5PO | Control | Nopol 5PO |
| Substitution, % BOTM | Rhodapex LA- | Rhodapex LA- | 7EO sulfate, | Rhodapex LA- | 7EO sulfate, |
| Total Surfactant | 40/S, 1.5% | 40/S, 1.5% | 1.5% | 40/S 1.5% | 1.5% |
| Surfactant B | Control | Control | Control | | |
| Substitution, % BOTM | Rhodasurf | Rhodasurf | Rhodasurf | Nopol 5PO | Nopol 5PO |
| Total Surfactant | 3065, 1% | 3065, 1% | 3065, 1% | 30EO, 1% | 30EO, 1% |
| Wet coagulum, % BOTL | 0 | 0 | 0 | 0 | 0 |
| Wet Grit, % BOTL | 0.09 | 0.07 | 0.26 | 0.38 | 0.28 |
| pH | 7.4 | 7.3 | 7.15 | 7.45 | 7.35 |
| Solids, % | 49.53 | 49.71 | 49.28 | 50.15 | 49.77 |
| Conversion, % | 95.91 | 96.29 | 93.02 | 96.6 | 96.33 |
| Particle Size | | | | | |
| Mean Diameter, nm | 149.8 | 159.63 | 184.6 | 148.17 | 186.06 |
| Std. Deviation, nm | 17.9 | 12.6 | 25.5 | 23.2 | 30.27 |
| Std. Deviation, % | 13.13 | 7.97 | 13.83 | 12.33 | 16.33 |
| Viscosity, 25° C., cP | 280 | 285 | 230 | 275.0 | 220 |
| Foam Test | | | | | |
| Initial Liquid volume, ml | 200 | 200 | 200 | 200 | 200 |
| Initial Foam Height, ml | 415 | 415 | 385 | 435 | 405 |
| Height after 5 minutes, ml | 415 | 415 | 385 | 435 | 405 |
| Height after 15 minutes, ml | 415 | 415 | 385 | 435 | 405 |
| Initial increase in volume, % | 108% | 108% | 93% | 118% | 103% |

BOTM = Based on total monomer
BOTL = Based on total liquid
nm = Nanometer
cP = Centipoise units
Rhodasurf 3065 is a commercially available alcohol ethoxylate (nonionic) from Rhodia.

Rhodapex LA-40/S is a commercially available sulfated alcohol ethoxylate (anionic) from Rhodia.

Table 9 shows the latex properties of the Example 3 formulations, which uses both an anionic surfactant (Surfactant A) and a nonionic surfactant (Surfactant B).

Anionic surfactants, such as sulfated alcohol ethoxylates, carry a negative charge. Nonionic surfactants, such as alcohol ethoxylates, have a neutral charge. Some latex formulations use both types of surfactant to optimize certain properties, such as stability and resistance to salts.

The results in Table 9 compare two commercially available standard surfactants to a Nopol PO/EO sulfate (anionic) and also a Nopol PO/EO (nonionic). In Trial # 30 the Nopol PO/EO sulfate is substituted for the control anionic surfactant. In Trial # 31 the Nopol PO/EO is substituted for the control nonionic surfactant. In Trial # 32, both Nopol surfactants were substituted for the control surfactants.

As illustrated in Table 9 similar latex properties were achieved with the Nopol based surfactants. Table 9 further illustrates that lower foaming properties were achieved by substituting the Nopol PO/EO sulfate for the control anionic surfactant.

The invention claimed is:
1. A latex composition comprising
   (A) an emulsion polymerizable unsaturated monomer;
   (B) water;
   (C) a free radical or redox initiator; and
   (D) a polymerization surfactant comprising at least one compound having a formula (I):

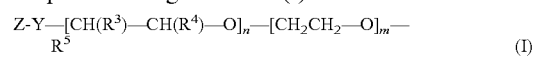

wherein Z represents a group having the following formula:

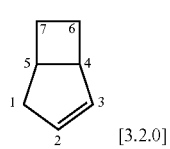

a)

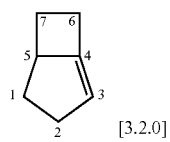

b)

-continued

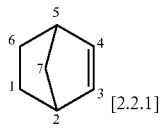 [2.2.1]

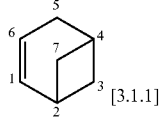 [3.1.1]

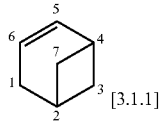 [3.1.1]

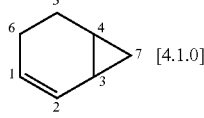 [4.1.0]

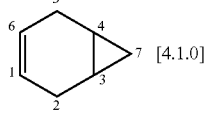 [4.1.0]

wherein:
- $R^3$ and $R^4$, which may be identical or different, represent hydrogen or a linear, branched or cyclic, saturated or unsaturated $C_1$-$C_{22}$ hydrocarbon radical, provided that at least one of the radicals $R^3$ $R^4$ other than hydrogen;
- $R^5$ is —$SO_3M$ or —$(CH_2)_z$—$SO_3M$;
- Y represents —$CH_2$—$C(R^1)(R^2)$—O— or —O—CH$(R'^1)$—$CH(R'^2)$—O—,
- wherein $R^1$, $R^2$, $R'^1$, and $R'^2$, which may be identical or different, represent hydrogen or a linear, branched or cyclic, saturated or unsaturated $C_1$-$C_{22}$ hydrocarbon radical;
- z is in the range of 1 to 6;
- M represents hydrogen, an alkali metal or an ammonium function $N(R)4+$, in which R, which may or may not be identical, represents hydrogen or a linear, branched or cyclic, saturated or unsaturated $C_1$-$C_{22}$ hydrocarbon radical, which may be hydroxylated;
- n is an integer or fractional number from 0 to 20 inclusive; and
- m is an integer or fractional number from 2 to 80 inclusive.

2. The latex composition of claim 1 wherein said compound has the formula:

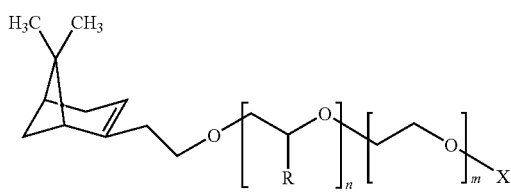

wherein X represents a sulfate or sulphonate group and R is hydrogen, $CH_3$ or $C_2H_5$.

3. The latex composition of claim 2 wherein said compound has the formula:

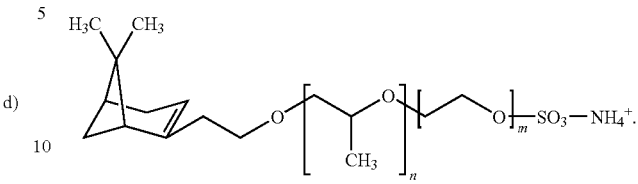

4. The latex composition of claim 1 wherein said polymerization surfactant is anionic.

5. The latex composition of claim 1 further comprising one or more additional surfactants selected from the group consisting of ionic surfactants, nonionic surfactants, or combinations thereof.

6. The latex composition of claim 1 wherein at least one of $R^1$, $R^2$, $R'^1$, or $R'^2$ represent a saturated or unsaturated $C_1$-$C_6$ hydrocarbon radical.

7. The latex of claim 1 in the form of a paint.

8. A process for the preparation of latex comprising the step of:
   emulsion polymerization of a reaction mixture comprising at least one unsaturated monomer, a free radical or redox initiator, and at least one compound having a formula (I):

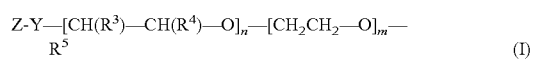

wherein Z represents a group having the following formula:

a)
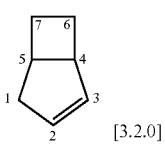 [3.2.0]

b)
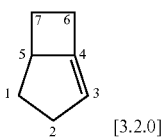 [3.2.0]

c)
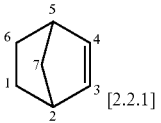 [2.2.1]

d)
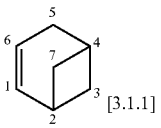 [3.1.1]

e)
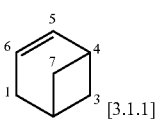 [3.1.1]

-continued

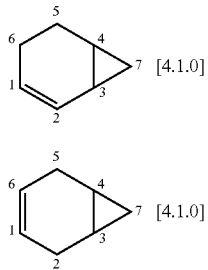

wherein:
- $R^3$ and $R^4$, which may be identical or different, represent hydrogen or a linear, branched or cyclic, saturated or unsaturated $C_1$-$C_{22}$ hydrocarbon radical, provided that at least one of the radicals $R^3$ $R^4$ other than hydrogen;
- $R^5$ represents —$SO_3M$, or —$(CH_2)_z$—$SO_3M$;
- Y represents —$CH_2$—$C(R^1)(R^2)$—O— or —O—CH$(R'^1)$—CH$(R'^2)$—O—, wherein $R^1$, $R^2$, $R'_1$, and $R'^2$, which may be identical or different, represent hydrogen or a linear, branched or cyclic, saturated or unsaturated $C_1$-$C_{22}$ hydrocarbon radical;
- z is in the range of 1 to 6;
- M represents hydrogen, an alkali metal or an ammonium function N(R)4+, in which R, which may or may not be identical, represents hydrogen or a linear, branched or cyclic, saturated or unsaturated $C_1$-$C_{22}$ hydrocarbon radical, which may be hydroxylated; and
- n is an integer or fractional number from 0 to 20 inclusive;
- m is an integer or fractional number from 2 to 80 inclusive.

9. The process of claim 8 further comprising the following steps:
   a) forming a stable aqueous pre-emulsion from an unsaturated monomer and the compound having formula (I),
   b) forming said reaction mixture comprising the pre-emulsion, an initiator, and water
   c) introducing the reaction mixture into a reactor and adding from 1 to 10% by weight of said pre-emulsion into to said reaction mixture, and
   d) heating said reaction mixture obtained at the end of step c) to a temperature of between 40° C. and 90° C. to generate a seed formed of latex particles in dispersion in the water.

10. The process of claim 9 further comprising
    e) reacting the seed formed of latex particles in dispersion in the water obtained in step d) with an additional amount of initiator to produce latex, and
    f) optionally, heating the latex obtained in step e) at a temperature of between 40° C. and 90° C.

11. The process of claim 9 wherein said monomer is selected from the group consisting of methyl acrylate, ethyl acrylate, methyl methacrylate, butyl acrylate, 2-ethyl hexyl acrylate, acrylates, methacrylates, acrylic acid, methacrylic acid, styrene, vinyl toluene, vinyl acetate, vinyl esters of higher carboxylic acids than acetic acid, vinyl versatate, acrylonitrile, acrylamide, butadiene, ethylene, vinyl chloride and mixtures thereof.

12. The process of claim 9 wherein said initiator is selected from the group consisting of ammonium persulfate, hydrogen peroxide, sodium, potassium, ammonium peroxydisulfate, dibenzoyl peroxide, lauryl peroxide, ditertiary butyl peroxide, 2,2'-azobisisobutyronitrile, t-butyl hydroperoxide, benzoyl peroxide, and mixtures thereof.

13. The process of claim 9 characterized in that 0.2% to 5% by weight of the compound having formula (I) with respect to the total weight of water is used during the polymerization.

14. The process of claim 13 characterized in that 1% to 4% by weight of the compound having formula (I) with respect to the total weight of water is used during the polymerization.

15. The process of claim 9 characterized in that 1% to 8% by weight of the compound having formula (I) with respect to the total weight of the monomers is employed during the polymerization.

16. The process of claim 15 characterized 2 to 5% by weight of the compound having formula (I) with respect to the total weight of the monomers is employed during the polymerization.

17. Building materials, paper, paints, adhesives or rheology modifiers comprising the latex prepared according to the process of claim 10.

18. The composition of claim 1 wherein said monomer is selected from the group consisting of methyl acrylate, ethyl acrylate, methyl methacrylate, butyl acrylate, 2-ethyl hexyl acrylate, acrylates, methacrylates, acrylic acid, methacrylic acid, styrene, vinyl toluene, vinyl acetate, vinyl esters of higher carboxylic acids than acetic acid, vinyl versatate, acrylonitrile, acrylamide, butadiene, ethylene, vinyl chloride and mixtures thereof.

* * * * *